United States Patent [19]
Cottrell et al.

[11] Patent Number: 5,847,230
[45] Date of Patent: Dec. 8, 1998

[54] NITRILE REMOVAL IN AN ETHERIFICATION PROCESS

[75] Inventors: Paul R. Cottrell; Ricardo Castillo, both of Arlington Heights, Ill.

[73] Assignee: UOP LLC, Des Plaines, Ill.

[21] Appl. No.: 859,299

[22] Filed: May 20, 1997

Related U.S. Application Data

[60] Provisional application No. 60/020,297 Jun. 24, 1996.
[51] Int. Cl.$^6$ .................................................. C07C 41/00
[52] U.S. Cl. .......................................... 568/699; 569/694
[58] Field of Search ..................................... 568/699, 694

[56] References Cited

U.S. PATENT DOCUMENTS

| | | | |
|---|---|---|---|
| 4,831,206 | 5/1989 | Zarchy | 585/737 |
| 5,120,881 | 6/1992 | Rosenfeld et al. | 568/697 |
| 5,260,493 | 11/1993 | Harandi et al. | 568/697 |
| 5,271,835 | 12/1993 | Gorawara et al. | 208/228 |
| 5,352,848 | 10/1994 | Cottrell | 568/699 |
| 5,569,790 | 10/1996 | Frey et al. | 568/599 |

*Primary Examiner*—Gary Geist
*Assistant Examiner*—J. Parsa
*Attorney, Agent, or Firm*—Thomas K. McBride; John G. Tolomei; Richard P. Silverman

[57] ABSTRACT

In an etherification process that uses an FCC effluent as a source of isoolefins, the buildup of nitrites in an alcohol-containing stream that is recycled to the etherification zone is prevented by dragging at least a portion of a water-containing stream produced by a water washing of the FCC effluent and returning the water-containing stream to the FCC gas concentration zone. As a result, the etherification catalyst deactivation rate is reduced and without increasing the net amount of fresh water employed by the process combination.

8 Claims, 1 Drawing Sheet

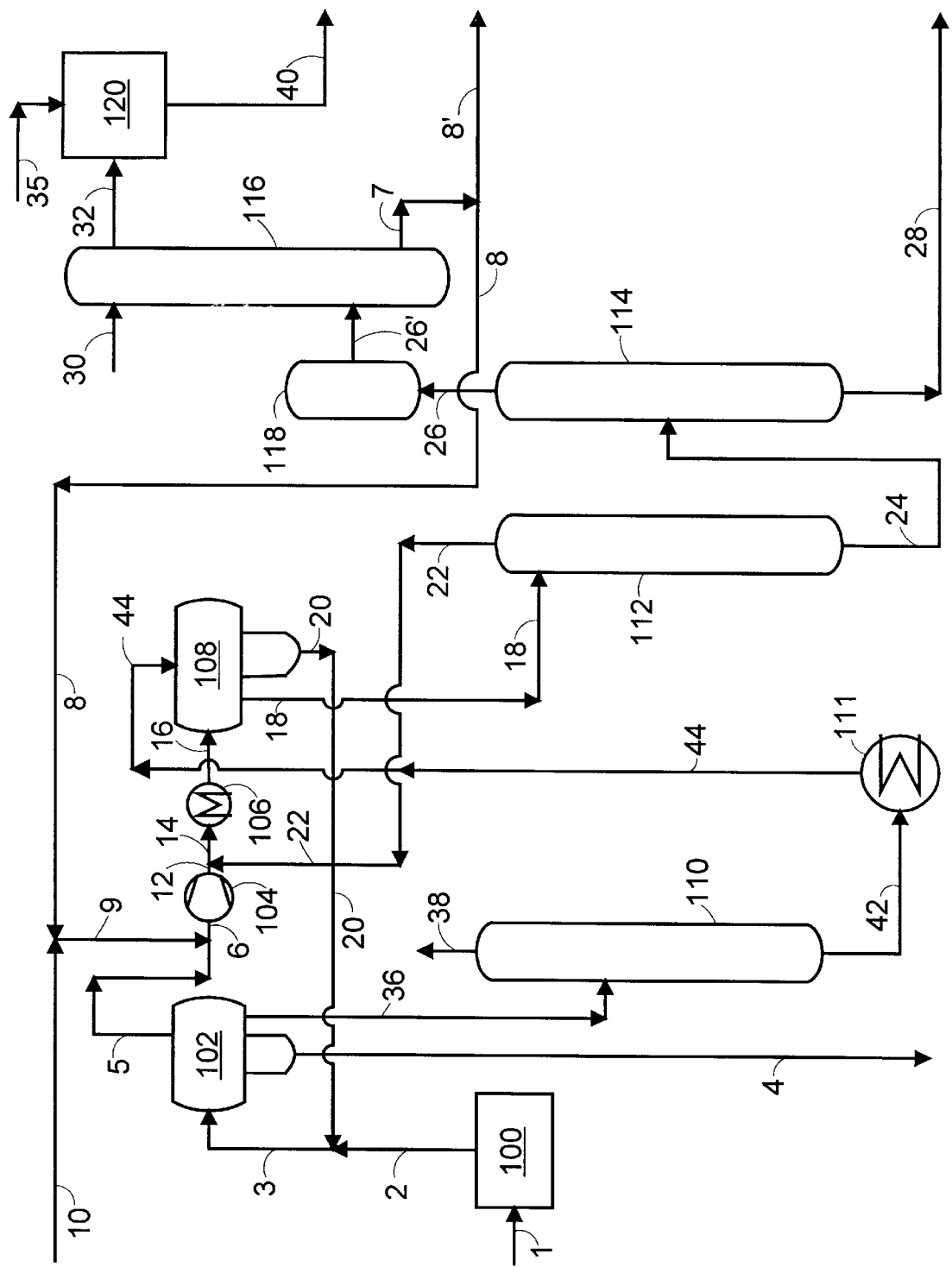

NITRILE REMOVAL IN AN ETHERIFICATION PROCESS

CROSS-REFERENCE TO RELATED APPLICATIONS

This application claims priority from copending Provisional Application No. 60/020,297, filed Jun. 24, 1996, hereby incorporated by reference.

FIELD OF THE INVENTION

This invention relates to a method of removing nitrites from a fluid catalytic cracking (FCC) effluent prior to contacting the FCC effluent with an alcohol in an etherification zone.

BACKGROUND OF THE INVENTION

Oxygenates, such as ethers, have been a part of the U.S. gasoline strategy since the late 1970's. These materials reduce carbon monoxide emissions and unburned hydrocarbons in the exhaust of internal combustion engines. Another advantage of oxygenates is that they have relatively good blending characteristics. Some oxygenates have better blending characteristics than others. For example, the blending vapor pressures of methyl tertiary butyl ether (MTBE), ethyl tertiary butyl ether (ETBE), tertiary amyl methyl ether (TAME), and tertiary amyl ethyl ethers (TAEE) are lower than methanol and ethanol, making them more attractive gasoline components.

MTBE or TAME can be produced by the addition of methanol to the corresponding isoolefin under etherification conditions. The reaction takes place in the presence of a catalyst at mild operating temperatures and pressures. The catalyst is usually a macrorectibular ion exchange resin based on a sulfonate styrene divinylbenzene copolymer.

It is not unusual for side reactions to occur during etherification reaction. For example, typical side reactions that can occur in an MTBE reactor include: (1) the formation of tertiary butyl alcohol (TBA) by isobutylene hydration; (2) the formation of di-isobutylene (DIB) by isobutylene dimerization; and (3) the formation of dimethyl ether (DME) and water by methanol dehydration.

Downstream processing of a the methyl tertiary butyl ether effluent usually includes separation of the ether products from the unconverted reactants, e.g., methanol. Effluent from the etherification reactor is usually passed to a fractionation tower where the methyl tertiary butyl ether product is removed from the bottom while side reaction products and unreacted reactants are separated as a raffinate overhead stream. The methanol contained in the raffinate is extracted with water by countercurrent, liquid-liquid extraction in a raffinate water wash tower. A methanol-containing stream leaves the bottom of the raffinate water wash tower and enters a methanol-water fractionation tower. A methanol-free raffinate stream leaves the top of the water wash tower and is directed to further downstream processing, e.g., alkylation. A water-containing stream free of methanol exits the bottom of the fractionation tower and is generally recycled for reuse in the raffinate water wash tower. A methanol-rich stream leaves the top of the fractionation tower and is recycled to the etherification reactor.

The most common source of isoolefinic hydrocarbons for use as a feedstock in an etherification process is the effluent from a fluid catalytic cracking (FCC) unit. FCC is a process for the conversion of straight-run atmospheric gas oil, vacuum gas oil, certain atmospheric residues, and heavy stocks recovered from other operations into high octane gasoline, light fuel oils, and olefin-rich light gases. In simplified terms, the cracking reactions are carried out in a vertical reactor vessel in which vaporized oil rises and carries along with it, in intimate contact, small fluidized catalyst particles. The reactions are very rapid, and only a few seconds of contact time are necessary for most applications. In a petroleum refinery, the FCC unit typically processes 30–50% of the crude oil charged to the refinery.

Early FCC units were designed to operate on vacuum gas oils directly fractionated from crude oils. Typically, these vacuum oils came from high quality crude oils. Today, much of the high quality feedstock for FCC units have been depleted and modern FCC units process less favorable materials. These less favorable materials include a substantial amount of sulfur compounds, metal cations, and nitrogen compounds. As a result, the contaminant levels in the FCC effluent have been growing, particularly in the $C_3$–$C_5$ effluent fraction. Without appropriate treatment, the contaminants in the $C_3$–$C_5$ FCC effluent fraction can be transmitted to sensitive downstream processes where they reduce the effectiveness of downstream catalysts and create unfavorable by-product reactions in processes such as etherification.

The use of FCC effluent as a feedstock for an etherification process can pose problems due to the above-described impurities. The FCC effluent stream usually contains a significant amount of metal cations that can deactivate the etherification ion exchange resin catalyst by plug flow neutralization. Plug flow neutralization occurs when a strong cation such as sodium reacts with sulfonic acid groups on the catalyst. This type of neutralization begins at the reactor inlet bed and slowly moves along the length of the reactor over a period of time. The FCC effluent will also contain some nitrogen compounds such as ammonia, light amines, dimethylformamide, N-methyl-pyrolydone, and nitrites having 1 to 3 carbon atoms, in particular propionitrile and acetonitrile (ACN).

Of particular concern are the nitriles, particularly the buildup of nitriles in the alcohol stream that is recycled back to the etherification reactor. The buildup of nitriles on the etherification catalyst will be a flat profile across the catalyst bed. In other words, unlike the basic nitrogenates such ammonia, the resin does not remove nitrites in a plug flow manner. As a result, in the case of nitrile contamination, the etherification catalyst continuously deactivates itself.

In the past, nitrogen compounds contained in FCC effluents bound for downstream hydrocarbon conversion processes were removed using complicated and expensive pretreatment systems, e.g., once through water wash or nitrogen removal units. The once through water wash approach uses a countercurrent, liquid-liquid tower wherein the FCC effluent is contacted with a high quality water-containing stream. Although from an equilibrium point of view the water wash should effectively remove the nitriles, the cost of the water wash system, which includes a large fractionation tower and a significant amount of fresh water, can be prohibitive.

A nitrogen removal unit (NRU) usually consists of a group of regenerable beds that adsorb the nitrites and other nitrogen components from the FCC effluent. The beds would be regenerated by an available regenerant determined for each unit. This regenerant can represent a problem in itself. The nitrogen components will be buried in the regenerant and must be removed or blended with another stream. If the regenerant is to be scrubbed, the cost of the materials and utilities required could be prohibitive. Blending the regenerant with gasoline could cause the blended gasoline product to develop color bodies or make the blended gasoline unstable. Examples of nitrogen removal units can be found in U.S. Pat. Nos. 4,831,206, 5,120,881 and 5,271,835 hereby incorporated by reference.

U.S. Pat. No. 5,352,848, hereby incorporated by reference, discloses an etherification process wherein the build-up of nitrites in an alcohol-containing stream is avoided by recycling at least a portion of the methanol-containing stream to an FCC reaction zone to reduce etherification catalyst deactivation.

There is a need for a method of removing nitrites from an FCC effluent that is used as a source of isoolefins in an etherification process that obviates the above-described problems of the prior art.

SUMMARY OF THE INVENTION

It has been discovered that over time a substantial amount of nitrites will build up in the alcohol-containing stream that is recycled to the etherification zone when an FCC effluent is used as the source of isoolefins. Left unchecked, the concentration of nitrites, particularly ACN, in the alcohol-containing recycle stream can multiply to 100 times the concentration of ACN entering the etherification zone in the FCC effluent. Such concentrations of nitrites can quickly deactivate the ion exchange resin etherification catalyst. Accordingly, the present invention drags at least a portion of the spent wash water stream from the once-thorough wash of the FCC effluent and employs at least a portion of the spent wash water stream in the gas concentration zone of the FCC process without increasing the overall wash water requirements while decreasing the amount of nitrites passed to the etherification zone. Surprisingly, it was found that the spent wash water produced by a once-through water wash of the etherification feedstream could be employed in the FCC gas concentration zone to effectively remove other contaminants such as sulfur compounds and/or oxygenates from the FCC effluent stream despite the presence of nitrites in the spent wash water. Consequently, the aforementioned buildup of nitrites in the alcohol-containing stream that is recycled to the etherification zone does not occur. Therefore, the deactivation rate of the etherification catalyst is decreased without incurring the sizeable capital and operating costs required for the previously-mentioned pretreatment systems.

The present invention is a process of treating an effluent of a fluid catalytic cracking zone, the FCC effluent stream comprising at least one nitrile compound which process comprises a series of steps:

The FCC effluent stream comprises nitrile compounds. The effluent stream is washed in a gas concentration zone comprising an absorption zone and a debutanizer zone with a first aqueous wash stream to produce a washed LPG stream comprising nitrile compounds. The washed LPG stream has a reduced amount of nitrile compounds relative to the FCC effluent stream from the FCC zone. The washed LPG stream is further washed in an etherification feed preparation zone. In the etherification feed preparation zone, the washed LPG stream is contacted with a second aqueous wash stream to produce a treated etherification zone feedstream and an aqueous extract stream. The treated etherification zone feedstream has a reduced amount of nitrile compounds relative to the effluent stream from the FCC zone. At least a portion of the aqueous extract stream is returned to the gas concentration zone to provide a portion of the first aqueous wash stream.

In one embodiment, the present invention is a process of treating an FCC effluent stream comprising $C_1$–$C_{10}$ hydrocarbons and at least one nitrile compound. The process comprises a series of steps. The FCC effluent stream is passed to an overhead receiver to produce a hydrocarbon vapor stream, a first hydrocarbon liquid stream, and a waste water stream. The hydrocarbon vapor stream is admixed with an aqueous wash stream to provide a first admixture. The first admixture is passed to a compressor zone to provide a compressed first admixture. The compressed first admixture and a stripper bottoms stream are passed to a high pressure receiver to produce a second hydrocarbon liquid stream and a high pressure water stream. The high pressure water stream is admixed with the FCC effluent stream prior to passing the FCC effluent stream to the overhead receiver. The first hydrocarbon liquid stream is passed to a stripping zone to provide a flue gas stream comprising $C_1$–$C_2$ hydrocarbons and the stripper bottoms stream. The second hydrocarbon stream is passed to an absorption zone to provide a first raffinate stream and an absorber bottoms stream. The absorber bottoms stream is passed to a debutanizer zone to produce an LPG effluent stream comprising $C_3$–$C_5$ olefinic hydrocarbons, nitrogen compounds, and an FCC gasoline stream comprising $C_4$–$C_{10}$ hydrocarbons. The LPG effluent stream is passed to an extraction zone wherein the LPG effluent is contacted with a wash water stream to provide a second raffinate stream and an aqueous extract stream. The second raffinate stream has a reduced amount of nitrile compounds relative to the LPG effluent stream. The aqueous extract stream comprises nitrile compounds. At least a portion of the aqueous extract stream is returned to the gas concentration zone to provide the aqueous wash stream. The second raffinate stream is passed to an etherification zone wherein the second raffinate stream and an alcohol stream are reacted in the presence of an etherification catalyst to produce an ether product.

DESCRIPTION OF THE DRAWING

The FIGURE is a schematic drawing of one embodiment of the present invention.

DESCRIPTION OF THE PREFERRED EMBODIMENT

The etherification feedstream of the present invention is an effluent from an FCC process. A typical feedstream will consist of a mixture of isobutane, isobutene, normal butane, 1-butene and 2-butene, 3,methyl-1-butene, isopentane, 1-pentene, 2,methyl-1-butene, normal pentane, trans-2-pentene, cis-2-pentene and 2,methyl-2-butene in a typical distribution of isomers.

Often the FCC effluent will contain diolefins in addition to the desired monoolefin feed components. These diolefins interfere with the operation of the catalyst in downstream processes by polymerizing and forming heavy hydrocarbons that block the active sites of the catalyst and prevent their use. In a preferred embodiment, the FCC effluent can undergo treatment for the elimination of diolefins. A common method of eliminating diolefins is by the selective hydrogenation of the olefins to saturate the diolefins into monoolefins. A particular catalyst and operating conditions for such selective dehydrogenation process can be found in U.S. Pat. Nos. 4,695,560 and 4,734,540, the contents of which are hereby incorporated by reference.

The selective hydrogenation process typically employs a nickel on aluminum catalyst or a noble metal, such as palladium on alumina, for selective hydrogenation. The nickel may be sulfided or unsulfided. The process can also operate in a broad range of operating conditions including pressures of from about 385 kPa to about 5.7 MPa (40–800 psig) with pressures of between about 450 kPa to about 2.2 MPa (50–300 psig) being preferred and temperatures of from about 21°–370° C. (70°–700° F.) with temperatures of from about 50°–200° C. (120°–400° F.) being preferred. Effective space velocities for the processes should be above 1 hr$^{-1}$ and preferably above 5 with a range of from about 5 to 35 hrs$^{-1}$. It is typical in such a process to limit the amount of hydrogen to prevent the saturation of monoolefins such that there is less than twice the stoichiometric amount of hydrogen required for the selective hydrogenation in the process. Preferably, the mole ratio of hydrogen to diolefinic hydrocarbons in the material will be in the range of from 1:1 to 1.8:1, and in some cases the hydrogen will be less than the stoichiometrically required amount of hydrogen.

The hydrocarbon feedstock of the present invention may also contain a variety of sulfur compounds. Generally, the feedstream contains about 1 to 5000 ppm by weight $H_2S$ and COS and, more typically, contains from about 1–1000 ppm by weight $H_2S$ calculated as elemental sulfur of the feedstock.

In one embodiment of the present invention, the hydrocarbon feedstock of the present invention is passed into an amine treating zone for $H_2S$ and COS removal. This amine treating zone employs alkanolamines selected from the group consisting of monoethanolamine (MEA), diethanolamine (DEA), methyldiethanolamine (MDEA), and mixtures thereof. The amine treating zone is operated over a temperature ranging from about 15°–66° C. (60°–150° F.) and a pressure ranging from about 100 kPa to about 3.5 MPa (15–500 psia). The amine treating will provide an $H_2S$-and COS-depleted stream which has been reduced by about 90% and, preferably, has been reduced by about 95% of the $H_2S$ and COS originally in the hydrocarbon feedstream.

In a preferred embodiment, the hydrocarbon feedstock of the present invention is passed to a mercaptan treating zone after amine treatment. In the mercaptan treating zone, the $H_2S$- and COS-depleted hydrocarbon feedstock is contacted with an alkaline scrubbing solution under mercaptan absorption conditions effective to produce a mercaptan-depleted stream and a mercaptide-containing scrubbing solution. The alkaline scrubbing solution may be selected from the group consisting of aqueous sodium hydroxide or aqueous ammonium hydroxide. The mercaptide-containing scrubbing solution is contacted with air or oxygen in the presence of an oxidation catalyst effective to regenerate the mercaptide-containing scrubbing solution. The temperature of the scrubbing solution ranges between about 10° C. and about 80° C., and, preferably, ranges between about 20° C. and a pressure generally in the range of about 100 kPa absolute to about 3450 kPa absolute in order to keep the $H_2S$- and COS-depleted stream in the liquid phase.

Additional information on the preferred mercaptan treating zone of the present invention can be found in U.S. Pat. Nos. 4,908,122 and 4,913,802 which are hereby incorporated by reference.

The hydrocarbon feedstream of the present invention will also contain nitrogen compounds including ammonia, light amines, dimethylformamide, N-methyl-pyrolydone, and nitriles having 1 to 3 carbon atoms, e.g., acetonitrile (ACN), propionitrile, and butylnitrile. It is the reduction of these nitrile compounds to which the present invention is directed, in particular ACN.

The feed to the process of the present invention includes an alcohol to react with the isoolefin and produce the desired ether product. The alcohols that can be used are typically $C_1$–$C_5$ monohydroxy alcohols. Methanol typically constitutes the alcohol of choice. Ethanol is also an alcohol that is suitable for use in the present invention.

In accordance with the present invention, the hydrocarbon feedstock of the present invention is passed to an etherification zone along with alcohol in the presence of a catalyst under etherification conditions. For the sake of simplicity, hereinafter the etherification process will be described in terms of MTBE; however, the etherification process of the present invention also includes the production of TAME, ETBE, and TAEE.

The isobutylene, as well as the normal butene, will enter the etherification zone along with methanol. Contact with an etherification catalyst at etherification conditions will produce the MTBE product. A wide range of materials is known to be effective as etherification catalysts for the MTBE reaction including mineral acids such as sulfuric acid, boron trifluoride, phosphoric acid on kieselguhr, phosphorous-modified zeolites, heteropoly acids, and various sulfonated resins. The use of a sulfonated solid resin catalyst is preferred. These resin-type catalysts include the reaction products of phenolformaldehyde resins and sulfuric acid and sulfonated polystyrene resins including those cross-linked with divinylbenzene. A particularly preferred MTBE catalyst is a macroporous acid-form of a sulfonic ion exchange resin such as a sulfonated styrene-divinylbenzene resin as described in U.S. Pat. No. 2,922,822 having a degree of cross-linking of about 5% to 60%. Suitable resins are available commercially. Specialized resins have been described in the art and include copolymers of sulfonyl fluorovinyl ether and fluorocarbons as described in U.S. Pat. No. 3,489,243.

Another specially prepared resin consists of the $SiO_2$modified cation exchangers described in U.S. Pat. No. 4,751,343. The macroporous structure of a suitable resin is described in detail in U.S. Pat. No. 5,012,031 as having a surface area of at least about 400 m$^2$/g, a pore volume of about 0.6–2.5 ml/g and a mean pore diameter of 40–1000 Angstroms. It is contemplated that the subject process could be performed using a metal-containing resin which contains one or more metals from sub-groups VI, VII or VIII of the Periodic Table such as chromium, tungsten, palladium, nickel, chromium, platinum, or iron as described in U.S. Pat. No. 4,330,679. Further information on suitable etherification catalysts may be obtained by reference to U.S. Pat. Nos. 2,480,940, 2,922,822, and 4,270,929.

A wide range of operating conditions are employed in processes for producing MTBE from isobutylene and methanol. Many of these include vapor, liquid, or mixed-phase operations. Processes operating with vapor or mixed phase conditions may be suitably employed in this invention. In a preferred embodiment, liquid phase conditions are used.

The range of etherification conditions for processes operating in liquid phase still includes a broad range of suitable conditions including a superatmospheric pressure sufficient to maintain the reactants as liquid phase, generally below about 700 psig, and a temperature between about 85° F. and about 210° F. Even in the presence of additional light materials, pressures in the range of about 140 to 580 psig are sufficient. A preferred temperature range is about 100° F.–210° F. The reaction rate is normally faster at higher temperatures, but conversion is more complete at lower temperatures due to favorable thermodynamics equilibrium. High conversion in a moderate volume reaction zone can, therefore, be obtained if the initial section of the MTBE reaction zone, e.g., the first two thirds, is maintained above 160° F. and the remainder of the MTBE reaction zone is maintained below 120° F. This may be accomplished most easily with two reactors. The ratio of methanol to isobutylene should normally be maintained in the range of about 1:1 to 2:1, and preferably, in the range of 1.05:1 and 1.5:1. An excess of methanol, above that required to achieve satisfactory conversion at good selectivity, should be avoided as some decomposition of methanol to dimethyl ether (DME) may occur which may increase the load on downstream separation facilities.

The MTBE reaction zone reacts selectively to principally convert only the isobutylene; therefore, butane and normal butene pass through the MTBE reaction zone without any significant conversion to products or by-products. Thus, the MTBE reaction zone effluent together with the unreacted isobutylene and methanol provide a stream of ether product and normal and branched butenes and butane isomers for separation.

The MTBE effluent exits the MTBE reaction zone and enters a separation zone. The separation zone can be any means known to those skilled in the art for separating a hydrocarbon stream into its various fraction. In a preferred embodiment, the arrangement of the separation zone consists of at least one distillation zone. In this distillation zone, a low boiling fraction comprising isobutane and methanol can be removed from the overhead stream of the distillation zone. In addition, the overhead stream can contain normal butene that was not reacted in the MTBE reaction zone and normal butane that entered the MTBE reaction zone as part of the hydrocarbon feedstream of the present invention. A high boiling fraction that principally comprises the MTBE product can be removed from the bottom portion of the distillation zone.

A useful arrangement for the separation zone of this invention is the use of a reactive distillation zone that contains a bed of etherification catalyst. The distillation zone can provide additional etherification of unreacted isobutene. Accordingly, the reactive distillation zone can be used as a combined reactor. Processes for the production of MTBE by reactive distillation are taught in U.S. Pat. Nos. 3,634,535 and 4,950,803. The operating conditions employed in the reactive distillation zone are generally the same as those outlined herein for the MTBE reaction zone. No particular apparatus or arrangement is needed to retain the catalyst bed within the distillation section of the reactive distillation zone and a variety of methods can be used to incorporate the bed or region of catalyst within the reactive distillation zone. For example, catalyst may be retained between suitable packing materials or may be incorporated onto a distillation tray itself. A preferred method of retaining the catalyst is through the use of a corrugated structural device that is described in U.S. Pat. No. 5,073,236 which is hereby incorporated by reference.

The MTBE product exits the bottom of the reactive distillation zone and is recovered. The overhead raffinate stream from the reactive distillation zone, comprising isobutane, normal butane, straight-chained butylene, a small amount of unreacted isobutylene, a small amount of unreacted methanol, DME, and TBA, is passed to a methanol recovery section.

The methanol recovery section may consist of a raffinate water wash zone and a methanol-water fractionation zone. In the raffinate water wash zone a water-containing stream enters the top of the zone and countercurrently contacts the overhead raffinate stream to remove methanol. Suitable operating conditions for the water wash zone include a temperature of about 100° F., a pressure of about 100 psi, and a water to methanol ratio of about 6 to 1. A hydrocarbon-rich raffinate stream having a methanol concentration of about 14 wt. % exits the raffinate water wash zone. This hydrocarbon-rich raffinate stream can be sent for further hydrocarbon processing, e.g., alkylation. A methanol-containing stream exits the bottom of the raffinate water wash zone.

In one embodiment of the present invention, the nitrile concentration in the methanol-containing stream is monitored, either intermittently or continuously. Based on the results of such monitoring, the nitrile concentration in the methanol-containing stream is then regulated by dragging that portion of the methanol-containing stream to the FCC reaction that is necessary to establish equilibrium conditions with the nitrile concentration entering the MTBE reaction zone in the FCC effluent.

The method used for monitoring the nitrile concentration in the methanol-containing stream that is recycled to the MTBE reaction zone can be any such method known to those skilled in the art. It is preferred that the method of monitoring the ACN concentration be capable of detecting nitrile concentrations as low as 1 mass ppm. A suitable method would be introducing a predetermined sample volume of the methanol-containing stream into a gas chromatograph that is equipped with a megabore fused silica capillary column that is internally coated with polyethylene glycol and a flame ionization detector.

Any FCC process known to those skilled in the art is suitable for use in the present invention. In a preferred embodiment, the reactor section of the FCC unit includes the features of dilute phase cracking in the riser and quick-quench cracking. Additional information regarding FCC unit process conditions and features suitable for use in the present invention can be found in Meyers, Robert A., *Handbook of Petroleum Refining Processes*, McGraw Hill, Inc. pages 2-9 to 2-32 (1986).

In the FCC process of the present invention, at least a portion of a water-containing stream from an etherification feed water wash zone is directed to the gas concentration section of the FCC unit and therein contacted with a portion of the FCC main column overhead stream to reduce the concentration of nitriles in the feed to the etherification zone. It is contemplated that nitrile removal from an FCC effluent stream used to feed an etherification zone can be reduced by passing at least a portion of or—under some circumstances—substantially all of the water-containing stream produced by an etherification feed water wash zone processing the FCC effluent stream and passing the water-containing stream to a disposal or consumption zone. Preferably, the water-containing stream is returned to the FCC gas concentration zone to replace, or at least partially offset, the requirement for wash water in an absorption zone in the FCC gas concentration zone. Suitable FCC feedstocks include, but are not limited to, straight-run atmospheric gas oils, vacuum gas oils, and certain atmospheric residues. The FCC catalyst can be any FCC catalyst known to those skilled in the art; preferably, it will be a zeolite-containing catalyst.

Once separated from the reactor section of the FCC unit, the hydrocarbon product vapor stream is passed to the gas concentration zone comprising a main column, an absorption zone, a stripping zone, and a debutanizer zone. Gasoline and gaseous olefin-rich co-products are taken overhead and routed to the gas concentration zone. In the gas concentration zone, the olefin-rich gas is compressed and directed through a series of absorbers, strippers, and fractionation towers to produce the FCC effluent of the present invention.

Referring to the figure, an FCC hydrocarbon gas oil feedstock enters an FCC reaction zone and main column zone 100 at line 1. A main column overhead stream exits the FCC section 100 via line 2. The main column overhead stream comprises $C_1$ to $C_{10}$ hydrocarbons, including $C_3$ and $C_5$ olefinic hydrocarbons, metal cations (such as sodium), nitrogen compounds such as ammonia and nitrites such as acetonitrile (ACN), and sulfur compounds such as $H_2S$, COS, and mercaptans.

The main column overhead stream is passed to a main column overhead receiver 102 via lines 2 and 3. The main column overhead receiver which is maintained at a temperature of about 25° C. (80° F.) to about 60° C. (140° F.) and a pressure of about 170 kPa (25 psia) to about 350 kPa (50 psia), and more preferably a pressure range of about 170 kPa to about 210 kPa, permits the separation of the main column overhead stream 3 into a waste water stream 4, a hydrocarbon vapor stream 5, and a first hydrocarbon liquid stream 36. The waste water stream 4 is withdrawn typically to a sour water stripper (not shown) for removal of impurities and disposal. The hydrocarbon vapor stream 5 admixed with a first aqueous wash stream 9 and the resulting first admixture is passed by line 6 to a compressor zone 104 to produce a compressed first admixture 12 at a pressure of about 1.37 MPa (195 psia) to about 1.65 MPa (235 psia). The compressed first admixture 12 is admixed with an adsorption zone raffinate 22 to provide a second admixture 14 and the second admixture 14 is passed to a high pressure receiver 108 along with a cooled stripper bottoms stream 44. The cooled stripper bottoms stream 44 was produced by passing the first hydrocarbon liquid stream 36 to a stripping zone 110 (reboiler not shown) wherein a flue gas stream 38, which may be used for fuel, was removed at the top of the stripping zone and a stripper bottoms stream 42 was removed from the bottom of the stripping zone. The stripper bottoms stream 42 is passed to a stripper bottoms cooler 111 to provide the cooled stripper bottoms stream 44. Returning to the high pressure receiver 108, a high pressure water stream 20 is passed in line 20 to be admixed with the main column overhead stream in line 2, and a second hydrocarbon liquid stream 18 is passed to an absorption zone 112 (reboiler not shown). In the absorption zone 112, which operates at a temperature ranging from about 35° C. to 60° C. and a pressure ranging from about 1.37 MPa to about 1.65 MPa, heavier hydrocarbon streams from the main column such as naphtha and light cycle oil (not shown) are employed as lean oil streams to absorb light ends and water to produce an absorber raffinate stream 22 and an absorber bottoms stream 24. The spent lean oil streams are returned to the main column or other product stripping columns in the gas concentration zone (not shown). The absorber raffinate stream 22 is admixed with the compressed first admixture 12 as described hereinabove. The absorber bottoms stream 24 is passed to a debutanizer zone 114 to provide an LPG effluent stream 26 comprising $C_3$–$C_5$ hydrocarbons and nitrile compounds such as acetonitrile and an FCC gasoline stream 28 comprising $C_4$–$C_{10}$ hydrocarbons. The FCC gasoline stream 28 is withdrawn for use in producing blends of high octane gasoline with ethers such as MTBE and other gasoline components such as reformate. The LPG effluent stream 26 may also comprise sulfur compounds, $H_2$, and COS. The LPG effluent stream 26 is passed to a sulfur treatment zone 118 wherein the sulfur compounds are removed from the LPG effluent stream 26. The sulfur treatment zone 118 comprises an amine treating unit for removing $H_2S$ and COS and a mercaptan treating unit for removing mercaptan compounds (both units not shown).

After desulfirizing the LPG effluent stream 26, a desulfurized effluent stream, or etherification feedstream 26', is withdrawn from the sulfur treatment zone 118 and passed to an etherification feed water wash zone 116 via line 26' to remove nitrile compounds such as acetonitrile. The etherification feedstream 26' is countercurrently contacted with a second aqueous wash stream 30 at a temperature of about 25° C. to about 40° C. to produce a treated etherification feedstream 32 having a reduced amount of nitrile compounds relative to the etherification feedstream 26' and an aqueous extract stream 7 enriched in nitrile compounds relative to the etherification feedstream 26'. Preferably, the treated etherification feedstream 32 comprises less than about 20 ppm-wt acetonitile and, more preferably, the treated etherification feedstream 32 comprises less than about 10 ppm-wt acetonitrile. Preferably, the rate of the fresh water stream, or the second aqueous wash stream, selectivity to the rate of the etherification feedstream is greater than about 30 percent of the rate of the etherification feedstream and, more preferably, the rate of the fresh water stream relative to the etherification feedstream ranges from about 30% to about 50% of the etherification feedstream. In order to remove the maximum amount of nitrites, it is preferred that the etherification feed water wash zone 116 be operated in with once-through or, essentially, all fresh wash water. Without limiting the scope of the invention, it is possible to achieve some of the benefits of the present invention by the recirculation of a portion of the aqueous extract stream within the etherification feed water wash zone. By the process of the present invention, the amount of nitrile compounds—specifically acetonitrile—in the feed to an etherification zone may be reduced returning at least a portion of and, preferably all of, the aqueous extract stream to the FCC gas concentration zone via lines 7, 8, and 9 as the first aqueous wash stream 9. The first aqueous wash stream is contacted with the hydrocarbon vapor portion of the main column overhead stream as described herein above. In an alternate operation, a portion of the aqueous extract stream may be withdrawn for disposal in line 8', offset with an equivalent amount of fresh water introduced in line 10.

The treated etherification feedstream 32 is passed to an etherification zone 120, for example, to produce an ether such as MTBE, ETBE, TAME, or TAEE by the reaction of an alcohol 35, such as methanol or ethanol, in the presence of an etherification catalyst to produce an ether product 40. The ether product having a high octane and a low vapor pressure is subsequently blended with other gasoline components such as FCC gasoline, reformate, and isomerate to produce high octane motor gasoline.

EXAMPLES

The following examples are provided for illustrative purposes and are not intended to limit the scope of the claims that follow. Example I is a illustrative example of a flow scheme which is representative of the prior art, conventional operation wherein the LPG effluent from an FCC is passed to an etherification feed water wash zone prior to passing the treated etherification feedstream to the etherification unit and none of the aqueous extract stream from the etherification feed water wash zone is combined with the water wash operations in the FCC gas concentration zone. Example II is illustrative of the present invention wherein the water wash rate in the etherification water wash zone is increased 16 fold and all of the resulting aqueous extract stream is returned to the FCC gas concentration zone. Surprisingly, the level of ACN in the treated etherification feedstream is reduced by 50% with no net increase in wash water leaving or entering the complex.

EXAMPLE I

A conventional etherification complex processes an FCC effluent stream comprising $C_3$–$C_5$ isoolefins and nitrile compounds such as ACN. According to the drawing, the scheme of Example I can be characterized by the passing of fresh wash water in line 30 separately to the etherification water wash zone 116 and disposing of the aqueous extract stream 7 via line 8'. In addition, a separate fresh water stream is introduced upstream of the compressor zone 104 in the FCC gas concentration zone via lines 10 and 9 and the waste water stream 4 is sent directly to disposal. Approximately 17 $m^3/hr$ of fresh water was required in the FCC gas concentration unit and about 1 $m^3/hr$ of fresh water was required in the etherification water wash zone 116 to provide a treated etherification zone feed stream 32 with an ACN concentration of about 40 ppm-wt. The etherification wash water column of Example I recirculated approximately 95% of the aqueous extract stream 7 within the etherification wash water column. About 26 $m^3/hr$ of waste water was produced in the scheme of Example I.

EXAMPLE II

Example II illustrates a combined operation of an FCC gas concentration unit and an etherification water wash zone, according to the process of the present invention wherein the aqueous extract stream 7 is employed as the fresh wash water in the FCC gas concentration zone. When the same FCC main column overhead stream 2 of Example I is employed and the water wash rate is increased to about 17 $m^3/hr$ in the etherification feed water wash zone 116 and when all of the aqueous extract stream 7 is returned via lines 7, 8, and 9 to the FCC gas concentration zone to recontact the overhead stream, surprisingly, the concentration of the ACN in the treated etherification feed drops about 18 ppm-wt of, or less than 50% of, the ACN concentration of Example I with no increase in the overall wash water requirement.

What is claimed:

1. A process for treating an FCC effluent stream comprising $C_1$ to $C_{10}$ hydrocarbons and at least one nitrile compound, said process comprising:
    a) passing said FCC effluent stream to an overhead receiver in an FCC gas concentration zone to produce a hydrocarbon vapor stream, a first hydrocarbon liquid stream, and a waste water stream;
    b) admixing said hydrocarbon vapor stream with an aqueous wash stream to provide a first admixture and passing said first admixture to a compressor zone to provide a compressed first admixture and passing said compressed first admixture and a stripper bottoms stream to a high pressure receiver to produce a second hydrocarbon liquid stream and a high pressure water stream and admixing said high pressure water stream with said FCC effluent stream prior to passing the FCC effluent stream to said overhead receiver;
    c) passing said first hydrocarbon liquid stream to a stripping zone to provide a flue gas stream comprising $C_1$–$C_2$ hydrocarbons and said stripper bottoms stream;
    d) passing said second hydrocarbon stream to an absorption zone to provide a first raffinate stream and an absorber bottoms stream and passing said absorber bottoms stream to a debutanizer zone to produce an LPG effluent stream comprising $C_3$–$C_5$ olefinic hydrocarbons and nitrile compounds, and an FCC gasoline stream comprising $C_4$–$C_{10}$ hydrocarbons;
    e) passing the LPG effluent stream to an extraction zone wherein said LPG effluent stream is contacted with a wash water stream to provide a second raffinate stream having a reduced amount of nitrile compounds relative to said LPG effluent stream and an aqueous extract stream comprising nitrile compounds;
    f) returning at least a portion of said aqueous extract stream to the FCC gas concentration zone to provide said aqueous wash stream and passing said second raffinate stream to an etherification zone wherein said second raffinate stream and an alcohol stream are reacted in the presence of an etherification catalyst to produce an ether product.

2. The process of claim 1 wherein said nitrile compound is selected from the group consisting of acetonitrile, propionitrile, and butylnitrile.

3. The process of claim 1 wherein said second raffinate stream comprises less than about 50 ppm acetonitrile.

4. The process of claim 1 wherein said second raffinate stream comprises less than about 20 ppm acetonitrile.

5. The process of claim 1 wherein at least about 50% of said aqueous extract stream is returned to provide a portion of said aqueous wash stream.

6. The process of claim 1 further comprising cooling said stripper bottoms prior to passing said stripper bottoms to said high pressure receiver.

7. The process of claim 1 further comprising cooling said compressed first admixture prior to passing said first admixture to said high pressure receiver.

8. The process of claim 1 further comprising admixing a portion of said ether product and said FCC gasoline stream to product a high octane gasoline stream.

* * * * *